(12) United States Patent
Gessler et al.

(10) Patent No.: US 6,713,097 B2
(45) Date of Patent: Mar. 30, 2004

(54) USE OF A PREPARATION OF CIMICIFUGA RACEMOSA

(75) Inventors: Andrea C. Gessler, Gleichen-Reinhausen (DE); Thomas Nisslein, Gottingen (DE)

(73) Assignee: Schaper & Brummer GmbH & Co. KG, Salzgitter (DE)

(*) Notice: Subject to any disclaimer, the term of this patent is extended or adjusted under 35 U.S.C. 154(b) by 24 days.

(21) Appl. No.: 10/239,888

(22) PCT Filed: Oct. 12, 2001

(86) PCT No.: PCT/DE01/03926
§ 371 (c)(1),
(2), (4) Date: Sep. 26, 2002

(87) PCT Pub. No.: WO02/36140
PCT Pub. Date: May 10, 2002

(65) Prior Publication Data
US 2003/0049340 A1 Mar. 13, 2003

(30) Foreign Application Priority Data
Nov. 3, 2000 (DE) .......................... 100 54 641

(51) Int. Cl.[7] .................................. A61K 35/78
(52) U.S. Cl. ........................ 424/773; 424/725
(58) Field of Search .................... 424/725, 773

(56) References Cited
FOREIGN PATENT DOCUMENTS
WO    WO 99/47149    9/1999

OTHER PUBLICATIONS

Brown, Jeanette S., et al., "Hysterectomy and urinary incontinence: a systematic review", The Lancet, vol. 356, pp535–539, (Aug. 12, 2000).

Thom, David H., et al., "Reproductive and Hormonal Risk Factors for Urinary Incontinence in Later Life: A Review of the Clinical and Epidemiologic Literature", JAGS, 46:1411–1417, (1998).

Liske, Eckehard. et al., "Therapeutic Efficacy and Safety of Cimicifuga Racemosa for Gynecologic Disorders", Advances in Therapy, vol. 15, No. 1, pp45–53, (Jan./Feb. 1998).

Kruse, Sven O., et al., "Fukiic and Piscidic Acid Esters from the Rhizome of Cimicifuga Racemosa and the in vitro Estrogenic Activity of Fukinolic Acid", Planta Medica, vol. 65, pp 763–764, (1999).

Einer–Jensen, N., et al., "Cimicifuga and Melbrosia lack oestrogenic effects in mice and rats", ISSN 0378–5122, vol. 25, No. 2 pp 149–153.

17th Edition—The Merck Manual of Diagnosis and Therapy, pp 1942–1943 (1999).

*Primary Examiner*—Leon B. Lankford, Jr.
*Assistant Examiner*—Susan Coe
(74) *Attorney, Agent, or Firm*—Whitman, Curtis & Christofferson, PC

(57) ABSTRACT

A preparation of *Cimicifuga racemosa* can be used to successfully treat urinary incontinence in female mammals following an ovariohysterectomy. Positive results can also be expected for the treatment of women following a hysterectomy or after the menopause.

9 Claims, No Drawings

USE OF A PREPARATION OF CIMICIFUGA RACEMOSA

The invention relates to the use of a preparation of *Cimicifuga racemosa* (Black Snakeroot), in particular an extract thereof, and more particularly an extract of the rhizome (*Rhizoma cimicifugae racemosae*).

Extracts of *Cimicifuga racemosa* are used in gyniatrics for the treatment of menopause complaints, such as hot flushes, sweating, sleep disorders, irritability, and depressive disgruntlement. The extract is regarded as a phytosubstitute for oestrogen replacement therapy. Extracts of *Cimicifuga racemosa* play no significant role in allopathic veterinary medicine.

It has been found, surprisingly, that preparations of *Cimicifuga racemosa* are therapeutically effective against urinary incontinence.

It is known that approximately 20% of bitches which have been subjected to castration, ie excision of the ovaries, and possibly also of the uterus, suffer from urinary incontinence as a secondary symptom of the operation after the elapse of approximately 2.7 years on average following ovariohysterectomy. The clinical symptoms are nowadays primarily treated with sympathomimetics, which, however, cause serious side effects in animals not optimally adjusted.

It was formerly assumed that this urinary incontinence was a result of the oestrogen deficiency induced by the operation. Despite doubts concerning such causality, aroused by the fact that the clinical picture does not occur prior to an elapse of an average of 2.7 years following ovariectomy, attempts have been made to treat the symptoms by oestrogen replacement. These doubts, combined with the side effects occurring during therapy have led to increased consideration of effecting treatment with sympathomimetics.

In women over 60 and having a basal incontinence incidence of from 10 to 33%, hysterectomy, ie the removal of the uterus but not the ovaries, ie without additionally influencing the hormonal status, raises the probability of developing urinary incontinence by 60%. Lesions caused by the operation on nerves and ligamentary connective tissue structures in the pelvic region are under discussion as being the cause of the problem (Lancet 2000; 356(9229): 535–539). Lesions of the same kind also commonly occur with the operative technique typically used in veterinary medicine. The effectiveness of the preparation of *Cimicifuga racemosa* of the invention for the treatment of urinary incontinence is thus not based on the properties hitherto ascribed to *Cimicifuga racemosa* as oestrogen substitute or as endocrinally active phytotherapeutic but rather on effects beyond known properties.

Although one must be cautious when considering applying veterinary causal and therapeutic findings to human syndromes, the results found suggest efficacy for the treatment of urinary incontinence in ovariectomized women or permenopausal or postmenopausal women. The occurrence of urinary incontinence in postmenopausal women is between 20 and 50% depending on age. No increase is observed in the perimenopause. Early oestrogen replacement is associated with slight symptom improvement on a short term basis only, whilst in the long run it is associated with an increase in the incontinence risk in women over 60, as has been shown in a published study (D. H. Thom, J. S. Brown in J. Am. Geriatr. Soc. 1998; 46(11): 1411–1417).

Thus the prior state of knowledge could not have suggested the presently proposed use of *Cimicifuga racemosa* for treatment of urinary incontinence and is unable to provide an explanation of the observed success thereof.

An effective daily dosage for the application proposed by the invention has been found to be a drug content of between 0.1 and 10 mg/kg of body weight. Thus it is advantageous to formulate an extract as tablets having a drug content of between 5 and 200 mg, and preferably between 10 and 50 mg, per tablet.

In the present invention, it is preferred to use an extract which has been prepared using an alcoholic extracting agent, particularly ethanol, isopropanol, or methanol.

Administration can be accomplished using any of the commonly used pharmaceutical administration forms, such as granules, capsules, suppositories, tablets, solutions, tea preparations, or by transdermal means, such as a plaster or the like.

It is also suitable as an additive for food or fodder.

The preparation must not necessarily be administered as an extract For example, it is possible to grind the plant or portions thereof for direct or indirect ingestion, for example, as tea.

Therapy involving the preparation of *Cimicifuga racemosa* as proposed in the invention is particularly suitably for female mammals following an ovariohysterectomy and for women following a hysterectomy or after the menopause.

EXAMPLE

Ovariectomized bitches showing the symptomatic complex of urinary incontinence were treated with an extract of *Rhizoma cimicifugae racemosae* in the form of tablets ("Remlfemin" tablets, sold by Schaper & Brummer GmbH & Co. KG). An effective daily intake of from one half to one whole tablet per 10 kg of body weight was used. In all of the fourteen cases treated there was remittence of the incontinence. The subjective judgement of the owners of the treated bitches on the therapeutic success and the compatibility of the pharmaceutical preparation was positive in all cases. In all cases, the owners asked for continuation of the therapy. In all cases there was distinct improvement of condition going, in some cases, as far as complete subsidence of the complaint.

The Remifemin® tablets used contain an extract of 20 mg of drug per tablet. The extracting agent used was isopropanol 40 vol %.

What is claimed is:

1. A method for treatment of urinary incontinence, comprising administering, to a patient, a preparation of *Cimicifuga racemosa*.

2. The treatment method of claim 1, wherein the preparation comprises an extract of *Cimicifuga racemosa*.

3. The treatment method as claimed in claim 2, wherein the extract has been produced using an alcoholic extracting agent.

4. The treatment method as claimed in claim 2, wherein the preparation is in the form of tablets having *Cimicifuga racemosa* content of between 5 and 200 mg per tablet.

5. The treatment method as claimed in claim 1, wherein an additive for supplemented fodder is administered.

6. The treatment method as claimed in claim 3, wherein the *Cimicifuga racemosa* administering is in the form of tablets having *Cimicifuga racemosa* content of between 5 and 200 mg per tablet.

7. The treatment method according to claim 1, wherein *Cimicifuga racemosa* is administered in a range of between 0.1 and 10 mg *Cimicifuga racemosa* per kg of body weight.

8. The treatment method according to claim 1, comprising *Cimicifuga racemosa* administration to one selected from the group consisting of: a female mammal following an ovariohysterectomy; a woman following a hysterectomy and a woman after menopause.

9. The treatment method of claim 1, wherein *Rhizoma cimicifugae racemosae* is administered.

* * * * *